United States Patent [19]

Kidani et al.

[11] Patent Number: 5,648,384

[45] Date of Patent: Jul. 15, 1997

[54] ANTI-TUMOR PLATINUM (IV) COMPLEX

[75] Inventors: Yoshinori Kidani, No. 13-11, Kataseyama 3-chome, Fujisawa-shi, Kanagawa; Yasunobu Komoda, Kanagawa, both of Japan

[73] Assignees: Tanaka Kikinzoku Kogyo K.K.; Yoshinori Kidani, both of Japan

[21] Appl. No.: 317,919

[22] Filed: Oct. 4, 1994

[30] Foreign Application Priority Data

Oct. 4, 1993 [JP] Japan .................... 5-271246
Oct. 4, 1993 [JP] Japan .................... 5-271247
Nov. 12, 1993 [JP] Japan .................... 5-307168

[51] Int. Cl.$^6$ .................... A61K 31/28; C07F 15/00
[52] U.S. Cl. .................... 514/492; 556/137
[58] Field of Search .................... 556/137; 514/492

[56] References Cited

U.S. PATENT DOCUMENTS 4,599,352  7/1986  Narayanan et al. .................... 514/492
5,288,887  2/1994  Khokhar et al. .................... 556/137

OTHER PUBLICATIONS

Siddik et al., Anti-Cancer Drug Design, vol. 9, No. 2, pp. 139–151, (Apr. 1994).
Siddik et al., J. Cancer Res. Clin. Oncol., vol. 120, No. 7, pp. 404–414, (May 1994).
Austin et al., Inorg. Chem., vol. 31, pp. 4281–4285 (1992).
Khokar et al., J. Inorg. Biochem., vol. 50, NO. 2, pp. 79–87 (May 1993).

*Primary Examiner*—Porfirio Nazario-Gonzalez
*Attorney, Agent, or Firm*—Klauber & Jackson

[57] ABSTRACT

Disclosed is an anti-tumor liposoluble platinum (IV) complexes having Formula I, a Formula VI or a Formula XII. Because these complexes have liposoluble groups, they are effective for various internal organ tumors or cancers.

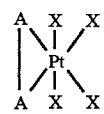

I

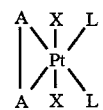

II

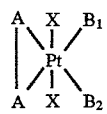

XIII

8 Claims, No Drawings

ANTI-TUMOR PLATINUM (IV) COMPLEX

BACKGROUND OF THE INVENTION

This invention relates to a novel anti-tumor platinum (IV) complex which may be liposoluble.

A certain kind of a platinum complex has been known to have an anti-tumor function, and such platinum complexes have been reported and been practically used. While, especially, a cis-dichlorodiammine platinum (II) complex (general name: cisplatine) and carboplatine are employed mainly for a spermary cancer, an ovarium cancer, a vesica cancer, a lung cancer and a cervix cancer, a platinum complex effective for the other organ tumors (for example, a brain tumor) other than the above cancers has seldom been reported. A platinum complex having a high specificity to a certain organ is desired.

Among the platinum complexes, a platinum (IV) complex of an isomer having a formula of $PtCl_4$-dach ("dach" designates cyclohexanediamine) has been expected to have new possibilities and reported U.S. Pat. No. 4,599,352, European Patent Publications Nos. 43490/77, 156659/78 and 13888/78, British Patent Publication Nos. 8328218 and 8028484).

However, all of these complexes are chlorinated ones, and they are not necessarily satisfactory in connection with the anti-tumor function in internal organs. No complexes other than chlorinated ones have been reported and their anti-tumor functions are unknown.

SUMMARY OF THE INVENTION

Accordingly, an object of the present invention is to provide a novel anti-tumor platinum complex which possesses more excellent anti-tumor characteristics than a conventional one, especially effective for internal organ tumors.

Another object of the present invention is to provide a novel anti-tumor platinum complex which may perorally administrated.

The liposoluble platinum (IV) complex of the present invention is, as mentioned later, excellent in anti-tumor characteristics, and because the complex is liposoluble, it is remarkably useful for recovering internal organ cancers in addition to the spermary cancer and the like.

Some of the complexes of the present invention have one or more liposoluble groups, for example, a carboxylic group having a long carbon chain, on its Z-axis to be more active against tumors.

It is pointed out that an anti-tumor complex which is effective for the internal organ cancers, especially for the brain tumor is required to have a high liposolubility. Because of the above liposoluble group, the complex of the present invention is considerably effective for various tumors or cancers.

DETAILED DESCRIPTION OF THE INVENTION

The present invention is an anti-tumor liposoluble halogenated platinum (IV) complex having a Formula I. In this Formula I, —A—A— designates one of the diamines of 1,2-cycloalkanediamine having a Formula II [n in the Formula II is 1, 2, 3 or 4, and its steric configuration is cis(R,S-), trans-d(1S,2S-) or trans-1(1R,2R-)], 2-aminomethylcyclohexylamine having a Formula III [in this Formula, its steric configuration is cis-1(R,R-), cis-d-(S,S-), trans-1(R,S-) or trans-d(S,R-)], 1,1-diaminomethylcyclohexane having a Formula IV, o-phenylenediamine, ethylenediamine and propyrenediamine, and X designates bromine, iodine or fluorine. The preferred diamine is 1,2-cyclohexanediamine having a Formula V.

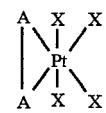

I

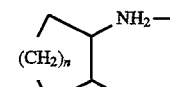

II

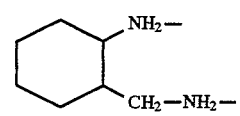

III

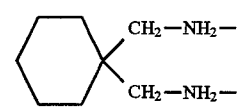

IV

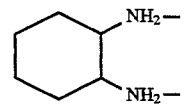

V

Another aspect of the present invention is a novel anti-tumor liposoluble platinum (IV) complex having a Formula VI. In this Formula VI, the symbol —A—A— has the same meanings as those of the Formula I, and the symbol —L—L— in the Formula VI designates a ligand forming a five or six-membered ring coordinating the platinum (IV) in the form of —O—O— coordination, and X designates one of carboxylate, carbonate, carbamate, sulfate and phosphate. The —L—L— is preferably oxalate having a Formula VII, 1,1-cyclobutane-dicaroxylate having a Formula VIII, a malonate having a Formula IX, a glycolate having a Formula X, a malonate derivative having a Formula XI or a glycolate derivative having a Formula XII.

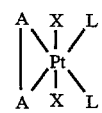

VI

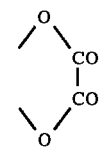

VII

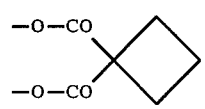

VIII

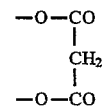

IX

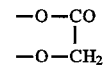

X

```
              -continued
            —O—CO                                XI
               |
              CHR
               |
            —O—CO

—O—CO                                XII
               |
            —O—CHR
```

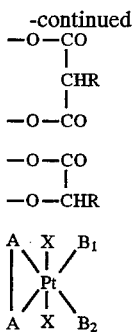

A further aspect of the present invention is a novel anti-tumor liposoluble platinum (IV) complex having a Formula XII. In this Formula XII, the symbol —A—A— has the same meanings as those of the Formula I, X designates bromine, iodine or fluorine, and $B_1$ and $B_2$ designate a ligand forming a five or six-membered ring coordinating the platinum (IV) in the form of —O—O— coordination.

EXAMPLES

Although the present invention will be described more in detail referring to Example, these Examples are not construed to restrict the present invention.

EXAMPLE 1

Synthesis of tetrabromo-1-dach-platinum (IV) complex (Formula XIV)

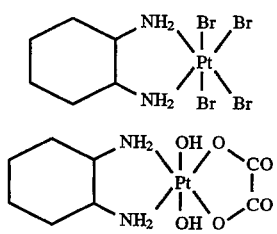

In 15 ml of ion exchange water, 1.50 g of dihydroxo-oxalato-1-dach-platinum (IV) complex (Formula XV) (3.48 mmol) was suspended. To this suspension, 3 ml of hydrobromic acid (47%) was added at 75° C. and reacted for 85 minutes. After 5 ml of water was further added to this suspension, which was then cooled at room temperature, a green precipitate was obtained upon filtration which was then washed with water. After the precipitate was dissolved in acetone for filtration of impurities, the filtrate was concentrated under vacuum to which hexane was added. The orange precipitate thus formed was collected by means of filtration and washed with hexane to obtain 0.65 g (30%) of tetrabromo-1-dach-platinum (IV) complex.

EXAMPLE 2

Synthesis of tetrabromo-d-dach-platinum (IV) complex (Formula XVI)

After 1.18 g (2.52 mmol) of dibromo-d-dach-platinum (II) complex (Formula XVI) was suspended in 67 ml of methanol, about 20 ml of a bromine-methanol solution (0.25 mmol/ml) was added at room temperature. After the lapse of one hour, the insoluble substances were removed by filtration and the filtrate was concentrated under vacuum. A crystal was collected by cooling the concentrated solution to 5° C. and filtrating the solution, and the crystal thus produced was washed with ether to obtain 1.07 g (88%) of tetrabromo-d-dach-platinum (IV) complex.

EXAMPLE 3

Synthesis of tetrabromo-cis-dach-platinum (IV) complex (Formula XVI)

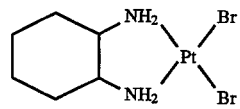

After 0.90 g of dibromo-cis-dach-platinum (II) (Formula XVI, 1.92 mmol) was suspended in 10 ml of methanol, 10 ml of a bromine (0.32 g, 2.0 mmol)-methanol solution was added to the suspension at room temperature. After the lapse of 90 minutes, orange precipitate produced was filtrated and washed with water. After the filtrated substance was dissolved in N,N-dimethyl formamide (DMF) to which small amounts of methanol and water were added, the solution was allowed to stand for two days. After a large amount of water was added, the orange precipitate was collected by means of filtration and washed with water to obtain 0.32 g (26%) of tetrabromo-cis-dach-platinum (IV) complex.

EXAMPLE 4

Synthesis of tetraiodo-1-dach-platinum (IV) complex (Formula XVII)

After 2.00 g (4.64 mmol) of dihydroxo-oxalato-1-dach-platinum (IV) (Formula XV) was suspended in 30 ml of ion exchange water, 4 ml of hydroiodic acid (57%) was added to this suspension without irradiation of lights at 70° C. and allowed to react for one hour. After the cooling to 5° C., the precipitate was collected by filtration and washed with water. After drying, 3.40 g (90° C.) of tetraiodo-1-dach-platinum (IV) complex was obtained.

EXAMPLE 5

Synthesis of tetraiodo-d-dach-platinum (IV) complex (Formula XVII)

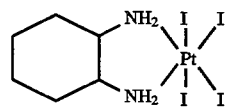

The same procedures as those of Example 4 were performed except that dihydroxo-oxalato-d-dach-platinum (IV) was employed in place of the dihydroxo-oxalato-1-dach-platinum (IV) of Example 4, to obtain 0.78 g (82%) of a tetraiodo-d-dach-platinum (IV) complex.

EXAMPLE 6

Synthesis of tetraiodo-cis-dach-platinum (IV) complex (Formula XVIII)

The same procedures as those of Example 4 were performed except that dihydroxo-oxalato-cis-dach-platinum (IV) was employed in place of the dihydroxo-oxalato-l-dach-platinum (IV) of Example 4, to obtain 0.79 g (83%) of a tetraiodo-cis-dach-platinum (IV) complex.

Elementary analysis and infrared absorption analysis of the compound synthesized in Examples 1 to 6 were carried out. The results thereof were shown in Tables 1 and 2. All of the said compounds were highly liposoluble.

TABLE 1

| Example | Molecular Formula (Molecular Weight) | Theoretical Value H | Theoretical Value C | Theoretical Value N | Measured Value H | Measured Value C | Measured Value N |
|---|---|---|---|---|---|---|---|
| 1 | $C_6H_{14}Br_4N_2Pt$(628.89) | 2.24 | 11.46 | 4.45 | 2.32 | 11.75 | 4.43 |
| 2 | " | " | " | " | 2.29 | 11.49 | 4.19 |
| 3 | " | " | " | " | 2.42 | 11.63 | 4.50 |
| 4 | $C_6H_{14}I_4N_2Pt$(816.89) | 1.73 | 8.82 | 3.43 | 2.00 | 8.94 | 3.39 |
| 5 | " | " | " | " | 1.99 | 9.07 | 3.26 |
| 6 | " | " | " | " | 1.88 | 9.08 | 3.51 |

TABLE 2

| Example | 1 | 2 | 3 | 4 | 5 | 6 |
|---|---|---|---|---|---|---|
| IR(cm−1) of N—H | 3160 | 3170 | 3175 | 3185 | 3180 | 3165 |

Anti-tumor properties of the complexes of Examples 1 to 6 against L1210, an experimental tumor of a mouse, were examined.

After L1210 (the number of implanted cells was $10^5$ per mouse) was transplanted in a $CDF_1$ mouse, the above complexes were administrated in its abdominal cavity at a first day, a fifth day and a ninth day.

The evaluation was determined by means of an average survival period propagation rate T/C (%) [(average survival days of administrated group)/(average survival days of reference group)×100]. For L1210, 125 or more is deemed effective, and the results thereof are shown in Table 3. One group consisted of six mice. The numbers in the brackets in Table 3 exhibits the numbers of the mice recovered.

TABLE 3

| Example | Average Surviving Period Propagation Rate T/C (%) [Administration Dose (mg/Kg)] | | | | | | | | |
|---|---|---|---|---|---|---|---|---|---|
| | 400 | 200 | 100 | 50 | 25 | 12.5 | 6.25 | 3.12 | 1.56 |
| 1 | | | | | | 0 | 235(1) | 250 | |
| 2 | | | | | 182(1) | 182(1) | 132 | | |
| 3 | | | | | 163(1) | 202(2) | 111 | | |
| 4 | | | 141 | 121 | 111 | | | | |
| 5 | | 107 | 109 | 105 | | | | | |
| 6 | | 111 | 109 | 90 | | | | | |

EXAMPLE 7

Synthesis of dibromo-oxalato-l-dach-platinum (Formula XVIII)

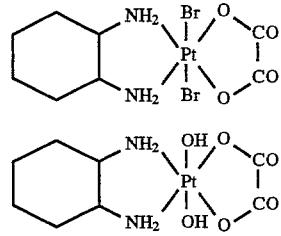

To 5.00 g (11.6 mmol) of dihydroxo-oxalato-l-dach-platinum (Formula XIX), 50 ml of ion exchange water and 4.41 g (23.2 mmol) of p-toluenesulfonic acid monohydrate were added at room temperature. After the mixture was shaken for completely dissolving the dihydroxo-oxalato-l-dach-platinum, the reaction solution was concentrated under vacuum and dried up. To this, 100 ml of ethanol was added and then 2.78 g (23.2 mmol) of potassium bromide was added at 5° C. and stirred for one hour. After the lapse of 80 minutes, a yellow precipitate was collected by filtration and dried with ion exchange water until the pH of the filtrate became neutral. The precipitate was further washed with ethyl acetate to obtain 2.98 g (43%) of dibromo-oxalato-l-dach-platinum as its dihydrate.

EXAMPLE 8

Synthesis of dibromo-oxalato-d-dach-platinum (Formula XX)

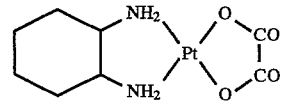

In 10 ml of ion exchange water was suspended 1.00 g (2.52 mmol) of oxalato-d-dach-platinum (Formula XX). To this suspension was added 10 ml of bromine water (0.26 mmol/ml) at 5° C. which was then vigorously shaken for 100 minutes. After the temperature was returned to room temperature, the reaction was kept to be continued for another 20 minutes and then again cooled to 5° C. After a yellow precipitate was collected by filtration and washed with water, the precipitate was dissolved in methanol for separating insoluble substances by filtration. When 30 ml of ion exchange water was added to the filtrate which was then concentrated under vacuum, a crystal begins to be formed, which was cooled to 5° C., was allowed to stand. The crystal was collected by filtration, and washed with water and dried to prepare 1.13 g (76%) of dibromo-oxalato-d-dach-platinum as its dihydrated compound.

EXAMPLE 9

Synthesis of diiodo-oxalato-l-dach-platinum (Formula XXI)

In 10 ml (2.52 mmol) of N,N-dimethetylformamide was suspended 1.00 g (2.52 mmol) of oxalato-l-dach-platinum (Formula XX), and 0.640 g (2.52 mmol) of iodine was added thereto at 70° C. After the lapse of about one hour, 10 ml of DMF was added to the above solution and insoluble substances were filtered. A crystal was collected by filtration upon addition of ethyl acetate to the filtrate, and the crystal was washed with ethyl acetate to obtain 1.52 g (76%) of diiodo-oxalato-1-dach-platinum. However, every two DMFs were contained in the respective molecules.

EXAMPLE 10

Synthesis of diiodo-oxalato-d-dach-platinum
(Formula XXI)

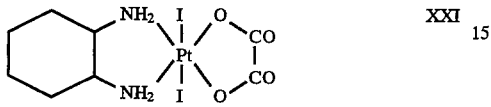
XXI

The same procedures as those of Example 9 were performed except that oxalato-d-dach-platinum was employed in place of the oxalato-1-dach-platinum of Example 9, to obtain 1.55 g (77%) of diiodo-oxalato-1-dach-platinum.

EXAMPLE 11

Synthesis of dibromo-malonate-1-dach-platinum
(Formula XXII)

In 10 ml of water was suspended 1.167 g (2.837 mmol) of malonate-1-dach-platinum (Formula XXII) to which 10 ml (2.88 mmol) of bromine water was added and thereafter vigorously agitated. After the lapse of 10 minutes, a yellow precipitate was collected by filtration and washed with water. The precipitate was dissolved in DMF for separating insoluble substances by filtration, and ethyl acetate was added thereto. The crystal produced was collected by filtration, and washed with ethyl acetate to obtain 0.42 g (25%) of dibromo-malonate-1-dach-platinum as its monohydrated compound.

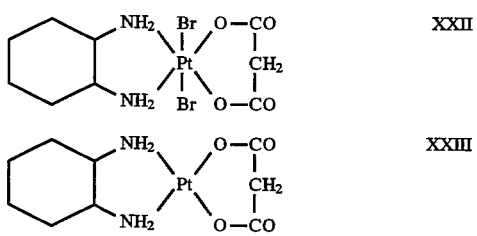

EXAMPLE 12

Synthesis of dibromo-malonate-d-dach-platinum
(Formula XXIV)

The same procedures as those of Example 11 were performed except that malonate-d-dach-platinum was employed in place of the malonate-1-dach-platinum of Example 11, to obtain 0.92 g (53%) of dibromo-malonate-d-dach-platinum.

Elementary analysis and infrared absorption analysis of the compound synthesized in Examples 7 to 12 were carried out. The results thereof were shown in Tables 4 and 5, respectively. All of the said compounds were highly lip-soluble.

TABLE 4

| Example | Molecular Formula (Molecular Weight) | Theoretical Value | | | Measured Value (%) | | |
|---|---|---|---|---|---|---|---|
| | | H | C | N (%) | H | C | N |
| 7 | $C_8H_{14}Br_2N_2O_4Pt \cdot 2H_2O$ (593.13) | 3.06 | 16.20 | 4.72 | 3.14 | 16.25 | 4.74 |
| 8 | " | " | " | " | 3.16 | 16.24 | 4.51 |
| 9 | $C_8H_{14}I_2N_2O_4Pt \cdot 2DMF$ (797.29) | 3.54 | 21.09 | 7.03 | 3.66 | 21.06 | 6.65 |
| 10 | " | " | " | " | 3.51 | 20.51 | 6.74 |
| 11 | $C_9H_{16}Br_2N_2O_4Pt \cdot H_2O$ (589.14) | 3.08 | 18.35 | 4.75 | 3.00 | 18.49 | 4.59 |
| 12 | " | " | " | " | 3.17 | 18.23 | 4.75 |

TABLE 5

| Example | 7 | 8 | 9 | 10 | 11 | 12 |
|---|---|---|---|---|---|---|
| IR($cm^{-1}$) of N—H | 3175 | 3170 | 3045 | 3045 | 3180 | 3180 |
| IR($cm^{-1}$) of C=O | 1710 | 1715 | 1715 | 1715 | 1660 | 1655 |

Anti-tumor properties of the complexes of Examples 7 to 12 against L1210, an experimental tumor of a mouse, were examined.

After L1210 (the number of implanted cells was $10^5$ per mouse) was transplanted in a $CDF_1$ mouse, the above complexes were administered in its abdominal cavity at a first day, a fifth day and a ninth day.

The evaluation was determined by means of an average survival period propagation rate T/C (%) [(average survival days of administrated group)/(average survival days of reference group)×100]. For L1210, 125 or more is deemed effective, and the results thereof are shown in Table G. One group consisted of six mice. The numbers in the brackets in Table 6 exhibits the numbers of the mice recovered.

TABLE 6

| Example | \multicolumn{9}{c}{Average Surviving Period Propagation Rate T/C (%) [Administration Dose (mg/Kg)]} |
|---|---|---|---|---|---|---|---|---|
|  | 400 | 200 | 100 | 50 | 25 | 12.5 | 6.25 | 3.12 | 1.56 |
| 7 |  |  | T92 | 263(3) | 288(3) |  |  |  |  |
| 8 |  |  |  | 175 | 132 | 134 |  |  |  |
| 9 |  | 91 | 105 | 201(1) | 273 |  |  |  |  |
| 10 |  | 0 | T194 | 134 |  |  |  |  |  |
| 11 |  |  |  | 247 | 209 | 131 |  |  |  |
| 12 |  |  |  | 228(1) | 185 | 176 |  |  |  |

EXAMPLE 13

Synthesis of Pt (oxalato)(OCOCH$_3$)$_2$(1-dach)
(Formula XXIV)

To 5.00 g (11.6 mmol) of Pt(oxalato)(OH)$_2$(1-dach) was added 50 ml (510 mmol) of acetic anhydride, which was then agitated at 70° C. for three hours. Thereafter, the reaction solution was concentrated and eventually dried up under vacuum.

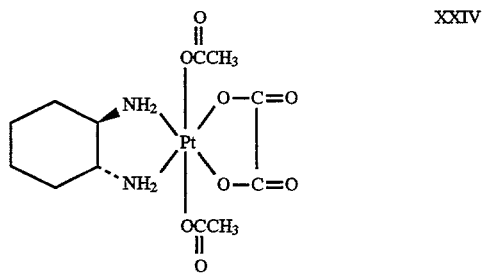

XXIV

Then, the dry residue was recrystallized from 60 ml of hot water to obtain 4.12 g (69%) of Pt(oxalato)(OCOCH$_3$)$_2$(1-dach).

EXAMPLE 14

Synthesis of Pt(oxalato)(OCOCH$_2$CH$_3$)$_2$(1-dach)
(Formula XXV)

To 4.00 g of Pt(oxalato)(OH)$_2$(1-dach) was added 40 ml of propionic anhydride, which was then agitated at 75° C. for 25 hours. After the solution was cooled to room temperature by standing, 250 ml of hexane was added to the solution, and a precipitate was collected by filtration. After the precipitate was washed with hexane and dissolved in methanol, insoluble substances were filtered and the filtrate was concentrated under vacuum.

Then, the residue was recrystallized from methanol-diethylether-petroleum ether to obtain 3.79 g (75%) of Pt(oxalato)(OCOCH$_2$CH$_3$)$_2$-(1-dach).

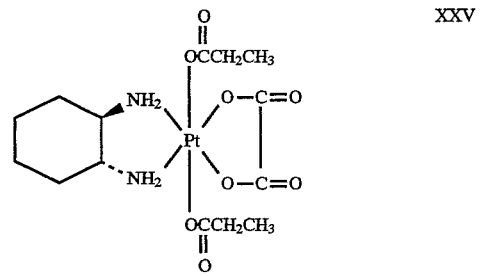

XXV

EXAMPLE 15

Synthesis of Pt(oxalato)[OCO(CH$_2$CH$_2$CH$_3$]$_2$(1-dach) (Formula XXVI)

To 7.00 g of Pt(oxalato)(OH)$_2$(1-dach) was added 70 ml of n-butyric anhydride. Thereafter, the same procedures as those of Example 14 were performed to obtain 5.47 g (57%) of Pt(oxalato)[OCO(CH$_2$)$_2$CH$_3$]$_3$(1-dach) as its monohydrate.

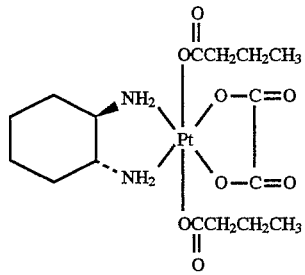

XXVI

EXAMPLE 16

Synthesis of Pt(oxalato)[OCO(CH$_2$)$_3$Ch$_3$]$_2$(1-dach)
(Formula XXVI)

To 1.00 g of Pt(oxalato)(OH)$_2$(1-dach) were added 5 of DMF and 5 ml of n-pentanoic anhydride, which were then agitated at 75° C. for 24 hours. After the solution was concentrated under vacuum, a large amount of hexane was added to the residue.

After the precipitate was collected by filtration and washed with hexane, it was isolated with a silica gel column chromatography (eluent: ethyl acetate). The isolated precipitated was recrystallized from methanol-diethylether to obtain 0.49 g (34%) of Pt(oxalato)-[OCO(CH$_2$)$_3$CH$_3$]$_2$(1-dach) as its monohydrate.

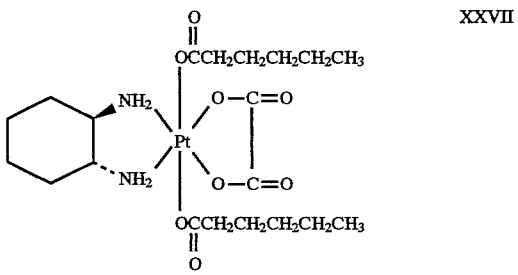

XXVII

EXAMPLE 17

Synthesis of Pt(oxalato)[OCO(CH$_2$)$_4$CH$_3$]$_2$(1-dach)
(Formula XXVI)

In accordance with the same procedures as those of Example 16 except that n-hexanoic anhydride and 10 ml of DMF were employed in place of the n-pentanoic anhydride and 5 ml of DMF, 0.83 g (57%) of Pt(oxalato) [OCO(CH$_2$)$_4$CH$_3$]$_2$(1-dach) was obtained.

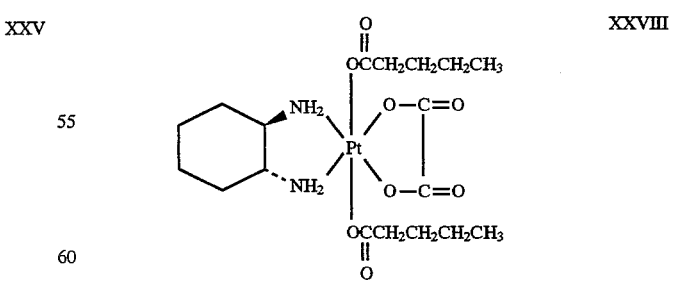

XXVIII

EXAMPLE 18

Synthesis of Pt(oxalato)[OCO(CH$_2$)$_5$CH$_3$]$_2$(1-dach)
(Formula XXIX)

In accordance with the same procedures as those of Example 16 except that 6 ml of n-heptanoic anhydride and 10 ml of DMF were employed in place of the n-pentanoic anhydride and 5 ml of DMF, 0.98 g (64%) of Pt(oxalato)[OCO(CH₂)₅CH₃]₂(1-dach) was obtained as its ½ hydrate.

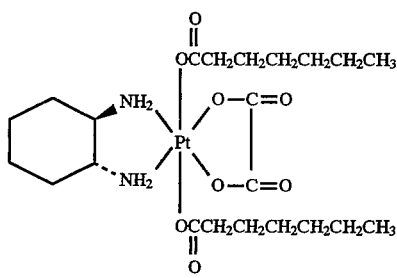

XXIX

EXAMPLE 19

Synthesis of Pt(oxalato)[OCO(CH₃)₆CH₃]₂(1-dach) (Formula XXX)

In accordance with the same procedures as those of Example 16 except that 6 ml of n-octanoic anhydride and 10 ml of DMF were employed in place of the n-pentanoic anhydride and 5 ml of DMF, 1.16 g (73%) of Pt(oxalato)[OCO(CH₂)₅CH₃]₂(1-dach) was obtained.

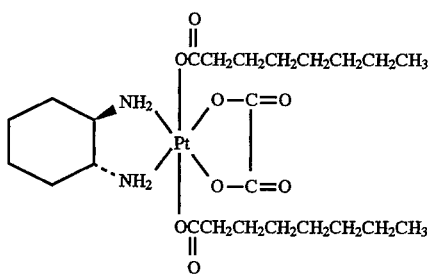

XXX

EXAMPLE 20

Synthesis of Pt(malonato) (OCOCH₃)₂(1-dach) (Formula XXXI)

To 1.00 g of Pt(malonato)(OH)₂(1-dach) was added 10 ml of acetic anhydride, which was then agitated at 70° C. for two hours and twenty minutes. After the solution was cooled to room temperature, a large amount of diethylether was added to cool the temperature to 5° C. The precipitate was collected by filtration and washed with ether. After the precipitate was dissolved in water and insoluble substances were filtered, the filtrate was concentrated under vacuum.

Then, the residue was recrystallized from methanol-water-diethylether to obtain 0.93 g (78%) of Pt(malonato)(OCOCH₃)₂(1-dach).

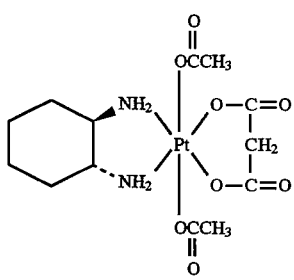

XXXI

EXAMPLE 21

Synthesis of Pt(malonato)(OCOCH₂CH₂)₂(1-dach) (Formula XXXII)

In accordance with the same procedures as those of Example 14 except that 300 mg of Pt(malonato)(OH)₂(1-dach), 3 ml of propionic anhydride and 3 ml of toluene as a solvent were employed in place of the 4.00 g of Pt(oxalato)(OH)₂(1-dach) and 40 ml of propionic anhydride, 351 mg (86%) of Pt(malonato)(OCOCH₂CH₃)₂(1-dach) was obtained as its 5/2 hydrate.

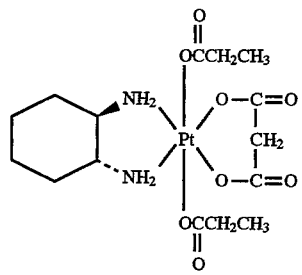

XXXII

EXAMPLE 22

Synthesis of Pt(malonato)[OCO(CH₃)₂CH₃]₂(1-dach) (Formula XXXII)

In accordance with the same procedures as those of Example 14 except that 1.00 g of Pt(malonato)(OH)₂(1-dach), 10 ml of n-butyric anhydride and 10 ml of toluene as a solvent were employed in place of the 4.00 g of Pt(oxalato)(OH)₂(1-dach) and 40 ml of propionic anhydride, 0.37 g (28%) of Pt(malonato)[OCO(CH₃)₂CH₃]₂(1-dach) was obtained as its ½ hydrate.

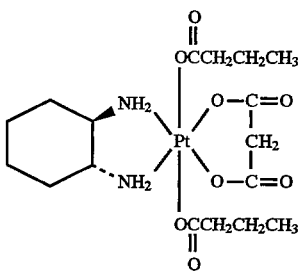

XXXIII

EXAMPLE 23

Synthesis of Pt(malonato)[OCO(CH₂)₃CH₃]₂(1-dach) (Formula XXXII)

In accordance with the same procedures as those of Example 16 except that 1.00 g of Pt(malonato)(OH)₂(1-dach), 5 ml of n-pentanoic anhydride and 10 ml of toluene as a solvent were employed in place of the 1.00 g of Pt(oxalato)(OH)₂(1-dach), 5 ml of DMF and 5 ml of n-pentanoic anhydride 0.35 g (25%) of Pt(malonato)[OCO(CH₂)₂CH₃]₂(1-dach) was obtained.

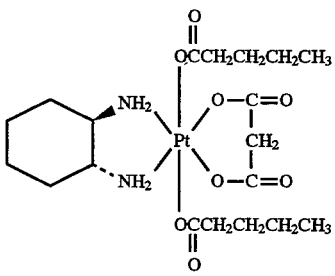

XXXIV

EXAMPLE 24

Synthesis of Pt(malonato)[OCO(CH$_2$)$_4$CH$_3$]$_2$(1-dach) (Formula XXXV)

In accordance with the same procedures as those of Example 16 except that 1.00 g of Pt(malonato)(OH)$_2$(1-dach), 5.5 ml of n-hexanoic anhydride and 10 ml of toluene as a solvent were employed in place of the 1.00 g of Pt(oxalato)(OH)$_2$(1-dach), 5 ml of DMF and 5 ml of n-pentanoic anhydride, 0.86 g (59%) of Pt(malonato)[OCO(CH$_2$)$_4$CH$_3$]$_2$(1-dach) was obtained as its ½ hydrate.

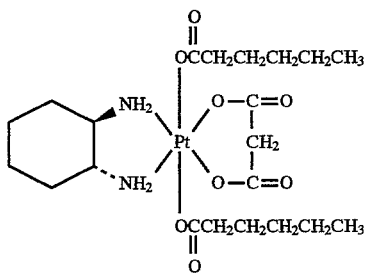

XXXV

EXAMPLE 25

Synthesis of Pt(malonato)[OCO(CH$_2$)$_5$CH$_3$]$_2$(1-dach) (Formula XXXVI)

In accordance with the same procedures as those of Example 16 except that 1.00 g of Pt(malonato)(OH)$_2$(1-dach), 4.5 ml of n-heptanoic anhydride and 10 ml of toluene as a solvent were employed in place of the 1.00 g of Pt(oxalato)(OH)$_2$(1-dach), 5 ml of DMF and 5 ml of n-pentanoic anhydride, 0.69 g (45%) of Pt(malonato)[OCO(CH$_2$)$_5$CH$_3$]$_2$(1-dach) was obtained as its ½ hydrate.

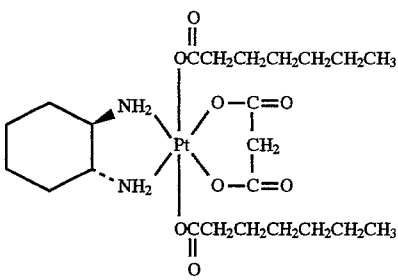

XXXVI

EXAMPLE 26

Synthesis of Pt(malonato)[OCO(CH$_2$)$_6$CH$_3$]$_2$(1-dach) (Formula XXXVII)

To 1.00 g of Pt(malonato)(OH)$_2$(1-dach) were added 10 ml of toluene and 5 ml of n-octanoic anhydride, which were then agitated at 75° C. for about 18 hours. After the toluene was distilled off, 10 ml of DMF was added to the residue and agitated at 75° C. for 1.5 hours.

Then, the DMF was distilled off and hexane was added to the residue which was then cooled to about −50° C. The precipitate was collected and isolated with a silica gel column chromatography (eluent, ethyl acetate:hexane =3:1). Thereafter, it was precipitated at about −70° C. from ethyl acetate-hexane to obtain 0.72 g (44%) of Pt(malonato)[OCO(CH$_2$)$_6$CH$_3$]$_2$(1-dach) in which ¼ molecule of the hexane was incorporated per one molecule of the platinum complex.

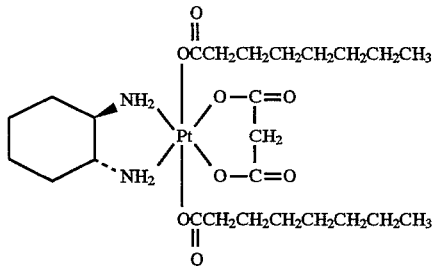

XXXVII

The analytical data of the compounds (complexes) prepared in Examples 13 to 26 are shown in Tables 7 and 8.

TABLE 7

| Example | Molecular Formula (Molecular Weight) | Theoretical Value H | C | N (%) | Measured Value (%) H | C | N |
|---|---|---|---|---|---|---|---|
| 13 | C$_{12}$H$_{20}$N$_2$O$_8$Pt(515.38) | 3.91 | 27.97 | 5.54 | 4.53 | 27.80 | 5.37 |
| 14 | C$_{14}$H$_{24}$N$_2$O$_8$Pt(543.43) | 4.46 | 30.94 | 5.16 | 4.64 | 31.10 | 5.26 |
| 15 | C$_{16}$H$_{28}$N$_2$O$_8$Pt.H$_2$O(589.50) | 5.13 | 32.60 | 4.75 | 4.93 | 32.39 | 4.76 |
| 16 | C$_{18}$H$_{22}$N$_2$O$_6$Pt.H$_2$O(617.56) | 5.55 | 35.01 | 4.54 | 5.49 | 35.30 | 4.66 |
| 17 | C$_{20}$H$_{30}$N$_2$O$_8$Pt(627.58) | 5.78 | 38.28 | 4.46 | 5.99 | 38.13 | 4.48 |
| 18 | C$_{22}$H$_{40}$N$_2$O$_8$.½H$_2$O(664.66) | 6.22 | 39.76 | 4.21 | 6.32 | 39.77 | 4.25 |
| 19 | C$_{24}$H$_{44}$N$_2$O$_8$Pt(683.70) | 6.49 | 42.16 | 4.10 | 6.79 | 42.19 | 4.00 |
| 20 | C$_{18}$H$_{22}$N$_2$O$_8$Pt(529.41) | 4.19 | 29.49 | 5.29 | 3.90 | 27.42 | 4.96 |
| 21 | C$_{16}$H$_{20}$N$_2$O$_8$Pt.½H$_2$O(602.50) | 5.19 | 29.90 | 4.65 | 4.95 | 29.75 | 4.71 |
| 22 | C$_{17}$H$_{30}$N$_2$O$_8$Pt.½H$_2$O(594.52) | 5.26 | 34.34 | 4.71 | 6.25 | 34.53 | 4.87 |
| 23 | C$_{19}$H$_{34}$N$_2$O$_8$Pt(613.57) | 5.59 | 37.19 | 4.57 | 5.68 | 37.11 | 4.60 |
| 24 | C$_{21}$H$_{42}$N$_2$O$_8$Pt.½H$_2$O(650.63) | 6.04 | 38.77 | 4.30 | 6.21 | 38.85 | 4.37 |
| 25 | C$_{23}$H$_{42}$N$_2$O$_8$Pt.½H$_2$O(678.68) | 6.39 | 40.70 | 4.13 | 6.54 | 40.90 | 4.12 |
| 26 | C$_{26}$H$_{48}$N$_2$O$_8$Pt.¼C$_6$H$_{14}$(719.27) | 6.94 | 44.25 | 3.89 | 6.94 | 44.25 | 3.89 |

TABLE 8

| Example | IR (cm⁻¹) N—H | C=O |
|---|---|---|
| 13 | 3030 | 1725, 1660 |
| 14 | 3155 | 1720, 1690 |
| 15 | 3200 | 1730 |
| 16 | 3150 | 1725 |
| 17 | 3190 | 1730 |
| 18 | 3160 | 1780 |
| 19 | 3130 | 1730 |
| 20 | 3180 | 1680, 1650 |
| 21 | 3150 | 1650 |
| 22 | 3050 | 1680, 1650 |
| 23 | 3050 | 1680, 1640 |
| 24 | 3100 | 1680 |
| 25 | 3100 | 1690 |
| 26 | 3050 | 1670, 1640 |

Anti-tumor properties of the complexes of Examples 13 to 26 against L1210, an experimental tumor of a mouse, were examined.

After L1210 (the number of implanted cells was $10^5$ per mouse) was transplanted in a $CDF_1$ mouse, the above complexes were administrated in its abdominal cavity at a first day, a fifth day and a ninth day.

The evaluation was determined by means of an average survival period propagation rate T/C (%) [(average survival days of administrated group)/(average survival days of reference group)×100]. For L1210, 125 or more is deemed effective, and the results thereof are shown in Table 9. One group consisted of six mice. The numbers in the brackets in Table 9 exhibits the numbers of the mice recovered.

TABLE 9

| | Average Surviving Period Propagation Rate T/C (%) [Administration Dose (mg/Kg)] | | | | | | | | |
|---|---|---|---|---|---|---|---|---|---|
| Example | 400 | 200 | 100 | 50 | 25 | 12.5 | 6.25 | 3.12 | 1.56 |
| 13 | | | 214(1) | 214 | 125 | 117 | 98 | | |
| 14 | | | 220 | 230(1) | 150 | 138 | 117 | | |
| 15 | | | 160(1) | 271(2) | 221 | 156 | | | |
| 16 | | 112 | 309(2) | 297(3) | | | | | |
| 17 | | 166 | 286(3) | 214(1) | | | | | |
| 18 | | 130 | 207(1) | 225(1) | | | | | |
| 19 | | 150 | 112 | 116 | | | | | |
| 20 | | 227(1) | 140 | 141 | 103 | 109 | | | |
| 21 | | 241(1) | 187 | 137 | 132 | 122 | | | |
| 22 | | 207 | 174 | 132 | | | | | |
| 23 | | 144 | 130 | 114 | | | | | |
| 24 | | 0 | 122 | 106 | | | | | |
| 25 | | 108 | 114 | 112 | | | | | |
| 26 | | 137 | 110 | 112 | | | | | |

What is claimed is:

1. An anti-tumor liposoluble halogenated platinum (IV) complex having a Formula I, wherein —A—A— in the Formula I is selected from the group consisting of the diamines of 1,2-cycloalkanediamine of the Formula II wherein n in the Formula II is 1, 2, 3 or 4, and its steric configuration is cis(R,S-), trans-d(1S, 2S-) or trans-1(1R, 2R-), 2-aminomethylcyclohexylamine of the Formula III wherein its steric configuration is cis-1(R,R-), cis-d-(S,S-), trans-1(R,S-) or tran-d(S,R-), 1,1-diaminomethylcyclohexane of the Formula IV, and X designates bromine, iodine or fluorine;

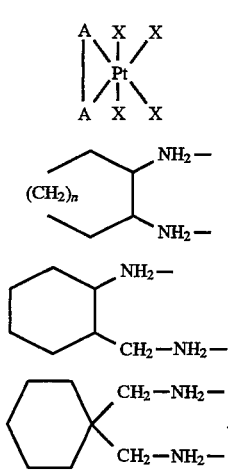

2. The anti-tumor liposoluble halogenated platinum (IV) complex according to claim 1, wherein —A—A— is a 1,2-cyclohexanediamine of the Formula V:

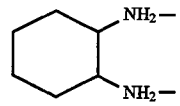

3. An anti-tumor liposoluble platinum (IV) complex of the Formula VI, wherein —A—A— in the Formula VI is selected from the group consisting of the diamines of 1,2-cycloalkanediamine of Formula II as defined in claim 1 wherein n in the Formula II is 1,2,3 or 4, and its steric configuration is cis(R,S-), trans-d(1S,2S-) or trans-1(1R,2R-), 2-aminomethylcyclohexylamine of the Formula III as defined in claim 1 wherein its steric configuration is cis-1(R,R-), cis-d(S,S-), trans-1(R,S-) or trans-d(S, R-), 1,1-diaminomethylcyclohexane of the Formula IV as defined in claim 1, and —L and —L in the Formula VI designate ligands forming a five or six-membered ring coordinating the platinum (IV) in the form of —O—O— coordination, and X is selected from the group consisting of carbonate, carbamate, sulfate and phosphate:

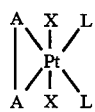

4. The anti-tumor liposoluble platinum (IV) complex according to claim 3, wherein —L—L— in the Formula VI is selected from the group consisting of oxalate of the Formula VII, 1,1-cyclobutane-dicarboxylate of the Formula VIII, malonate of the Formula IX, glycolate of the Formula X, a malonate derivative of the Formula XI and a glycolate derivative of the Formula XI:

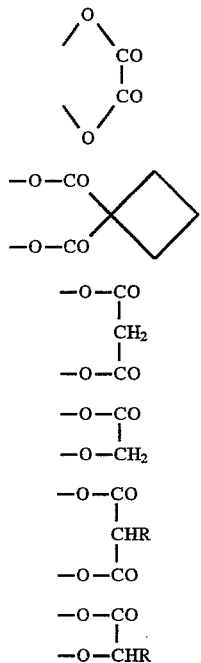

VII

VIII

IX

X

XI

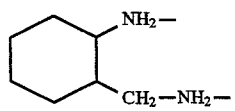

XII

5. The anti-tumor liposoluble platinum (IV) complex according to claim 3, wherein —A—A— is a 1,2-cyclohexanediamine of the Formula V.

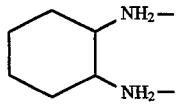

6. An anti-tumor liposoluble platinum (IV) complex having a Formula XI, wherein —A—A— in the Formula XI is selected from the group consisting of the diamines of 1,2-cycloalkanediamine of the Formula II

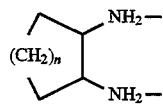

wherein in the Formula II is 1, 2, 3 or 4, and its steric configuration is cis(R,S-), trans-d(1S,2S-) or trans-1(1R,2R-), 2-aminomethylcyclohexylamine of the Formula III,

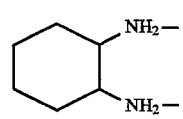

wherein its steric configuration is cis-1(R,R-), cis-d(S,S-), trans-1(R,S-) or trans-d(S,R-), 1,1-diaminomethylcyclohexane of the Formula IV,

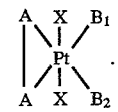

o-phenylenediamine, ethylenediamine and propylenediamine and $B_1$ and $B_2$ in the Formula XI designate a ligand forming a five or six-membered ring coordinating the platinum (IV) in the form of —O—O— coordination, and X is bromine, iodine or fluorine:

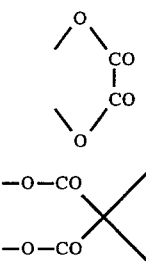

XIII

7. The anti-tumor liposoluble platinum (IV) complex according to claim 6, wherein the ligand formed by the $B_1$ and $B_2$ in the Formula XI is selected from the group consisting of oxalate of the Formula VII, 1,1-cyclobutane-dicarboxylate of the Formula VIII, malonate of the Formula IX, glycolate of the Formula X, a malonate derivative of the Formula XI and a glycolate derivative of the Formula XI.

VII

VIII

IX

X

XI

XII

8. The anti-tumor liposoluble platinum (IV) complex according to claim 7, wherein —A—A— is a 1,2-cyclohexanediamine of the Formula V.

* * * * *